United States Patent [19]

Suh et al.

[11] Patent Number: 4,696,939
[45] Date of Patent: Sep. 29, 1987

[54] BENZOTHIADIAZOLE COMPOUNDS FOR TREATING HYPERTENSION

[75] Inventors: John T. Suh, Greenwich, Conn.; John J. Piwinski, Parsippany, N.J.; Howard Jones, Ossining, N.Y.; Edward S. Neiss, New Canaan, Conn.

[73] Assignee: USV Pharmaceutical Corporation, Tuckahoe, N.Y.

[21] Appl. No.: 802,921

[22] Filed: Nov. 29, 1985

Related U.S. Application Data

[62] Division of Ser. No. 584,576, Feb. 29, 1984, Pat. No. 4,576,941.

[51] Int. Cl.$^4$ ............... A61K 31/41; C07D 285/14
[52] U.S. Cl. .................................. 514/361; 514/229; 514/309; 514/310; 514/312; 514/313; 514/338; 544/12; 544/135; 544/287; 546/141; 546/143; 546/153; 546/162; 546/271; 548/126; 548/359
[58] Field of Search ............... 548/126; 546/141, 143, 546/153, 162, 271; 544/135; 514/229, 309, 310, 312, 313, 338, 361

[56] References Cited

U.S. PATENT DOCUMENTS

| | | | |
|---|---|---|---|
| 4,256,761 | 3/1981 | Suh et al. | 424/282 |
| 4,338,435 | 7/1982 | Haugwitz | 544/13 |
| 4,431,644 | 2/1984 | Smith et al. | 424/246 |
| 4,431,645 | 2/1984 | Smith et al. | 424/246 |
| 4,468,396 | 8/1984 | Magatti | 424/246 |
| 4,482,725 | 11/1984 | Ondetti et al. | 548/533 |

*Primary Examiner*—Glennon H. Hollrah
*Assistant Examiner*—James H. Turnipseed

[57] ABSTRACT

Compounds of the formula

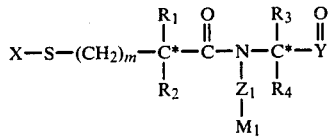

and their pharmaceutically acceptable salts, wherein the substituents are as defined herein, having antihypertensive activity.

11 Claims, No Drawings

BENZOTHIADIAZOLE COMPOUNDS FOR TREATING HYPERTENSION

This application is a division of our prior copending application Ser. No. 584,576, filed Feb. 29, 1984 now U.S. Pat. No. 4,576,941.

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula

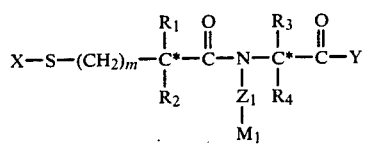   (1)

and pharmaceutically acceptable alkali metal, alkaline earth metal, and acid addition salts thereof, wherein X is hydrogen or

wherein A is alkyl, phenyl, or phenyl substituted with up to 3 substituents selected from the group consisting of halo, alkyl having up to 7 carbon atoms, —CF$_3$, OH, COOH, NH$_2$, and SO$_2$NH$_2$;

m is 0 to 3 inclusive;

Y is —OR or —N(R)R;

R$_1$, R$_2$, R$_3$ and R$_4$ are independently R or aminoalkyl,

Z$_1$, reading toward the M$_1$ substituent, is selected from the group consisting of —(CH$_2$)$_n$—, —N(R)CH$_2$(CH$_2$)$_n$—, —N(R)CH$_2$(CH$_2$)$_n$NH—, —(CH$_2$)$_n$SO$_2$—, —(CH$_2$)$_n$N(R)SO$_2$—, —(CH$_2$)$_n$—N(R)—, —(CH$_2$)$_n$N(R)C(O)—, —(CH$_2$)$_n$C(O)N(R)—, or —(CH$_2$)$_n$C(O)—, in which n is 0 to 6 inclusive, and one of the (CH$_2$) groups can be mono- or disubstituted with methyl or ethyl;

M$_1$ is independently selected from the group consisting of aryl, fused polycyclic aryl, heteroaryl, fused heterocyclic-aryl, and fused cycloalkylaryl, wherein up to 3 carbon atoms of M$_1$ can be oxidized to —C(O)— or replaced by —N(R)—, —O—, —S—, or —SO$_2$—; wherein M$_1$ has two or three substituents selected from the group consisting of halogen, alkyl, aminoalkyl, aralkyl, cycloalkyl, alkylamino, acylamino, acylaminoalkyl, acylaminoalkylamino, trifluoromethyl, nitro, cyano, —OR, —SR, —C(O)OR, —S(O)R, —SO$_2$R, —C(O)N(R)R, —N(R)R, or —SO$_2$N(R)R;

wherein in each occurrence R is independently hydrogen, alkyl, cycloalkyl, aryl, aralkyl, heteroalkyl, heteroaralkyl, or heteroaryl;

wherein the alkyl groups and the alkyl moieties contain up to 7 carbon atoms, the cycloalkyl and heterocyclic groups and moieties are saturated or unsaturated and contain 3 to 12 atoms, and the aryl and heteroaryl rings contain up to 12 atoms.

DESCRIPTION OF THE PREFERRED EMBODIMENTS

Preferred compounds of the present invention include those of the general formula given above in which Y is hydroxy, benzyloxy, or lower alkoxy; R$_1$, R$_2$, R$_3$ and R$_4$ are each hydrogen, alkyl, aryl, aralkyl, cycloalkyl, or w-amino ("omega-amino")alkyl wherein the amino is unsubstituted or mono- or disubstituted with alkyl, aryl, or aralkyl, or is incorporated in a saturated or unsaturated one- or two-ring heterocyclic moiety containing preferably up to 12 atoms in the ring; m is 1 or 2; and A is lower alkyl, lower cycloalkyl, or phenyl. More preferably, R$_2$ and R$_4$ are hydrogen; and R$_1$ and R$_3$ are each hydrogen or lower alkyl.

The alkyl groups per se and the alkyl moieties in alkoxy, aralkyl, cycloalkyl, aminoalkyl, and the like, may be straight-chained or branched and preferably contain from 1 to 7 carbon atoms. Such groups include methyl, ethyl, propyl, isopropyl, butyl, isobutyl, tertiary-butyl, amyl, iso-amyl, hexyl, and the like. Preferably the alkyl groups are lower alkyl, which term shall refer to alkyl groups containing from 1 to 4 carbon atoms, straight-chained or branched. The preferred substituents for lower alkyl include amino, —OH, —CONH$_2$, —OR, and —SR. The cycloalkyl groups and moieties are saturated or unsaturated and contain 3 to 12 carbon atoms and preferably 3 to 9 carbon atoms.

Preferred structures for Z$_1$ include a chemical bond and an alkylene bridge —(CH$_2$)$_n$— in which n is 0, 1, 2, 3, or 4.

Preferred cyclic and polycyclic ring structures contain up to 20 carbon atoms and include such radicals as cyclopropyl, cyclobutyl, cyclopentyl, cyclohexyl, cycloheptyl, adamantyl, norbornyl, phenyl, tolyl, benzyl, phenethyl, indolyl, indolinyl, hydroxybenzyl, indanyl, naphthyl, tetrahydronaphthyl, decanhydronaphthyl, pyridyl, quinolyl, isoquinolyl, guanidino, pyrrolidyl, pyrrolyl, morpholinyl, furyl, furfuryl, tetrahydrofurfuryl, benzimidazolyl, thienyl, imidazolyl, tetrahydroisoquinolyl, and the like, specifically including all isomers of radicals named herein that have more than one isomer.

M$_1$ is phenyl, fused aryl-cycloalkyl, or fused polycyclic aryl in which the aryl group or moiety carries two or three substituents other than hydrogen. One, two or three of the carbon atoms anywhere in M$_1$ can be —C(O)—, or replaced by —SO$_2$, —N(R)—, —O—, or —S—. Preferred structures include phenyl, indanyl,

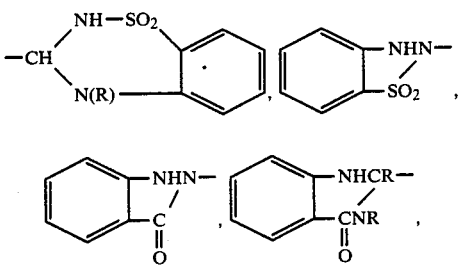

and benzimidazolyl. Preferred substituents for the aryl ring include halogen, nitro, lower alkyl, —COOH, carboxy-lower alkoxy, phenoxy, and hydroxy; sulfamoyl which is optionally substituted with alkyl; and amino which is optionally substituted with lower alkyl, phenyl, phenyl-lower alkyl, heteroaryl-lower alkyl, nitro-lower alkyl, lower alkyl-carbonyl, and lower alkyl-carbonyl-amino-alkyl, (e.g., $CH_3C(O)NH(CH_2)_{2-4}NH-$, $CH_3C(O)NH-$, and furfurylamino). The $M_1$ group is preferably connected to the main chain by non-labile bonds, so that the molecule (1) resists cleavage in the stomach and is thus intact when it enters the blood, which enhances the therapeutic effect and duration of the compound and may reduce undesirable side-effects.

The halo groups include fluoro, chloro, bromo and iodo. Preferred hetero atoms are S, O, and N. Preferred acyl groups are lower alkyl-carbonyl, and benzoyl.

Compounds in accordance with the present invention are readily prepared employing known starting materials and procedures. It will be understood by those skilled in the art that the carbon atoms denoted as C* in formula (1) can be asymmetric centers, such that the inventive compounds may exist in (R,R), (R,S), (S,R), and (S,S) forms. Individual isomers and diastereo-isomeric mixtures of said forms are within the scope of the invention. The preferred forms have the (S) or (S,S) configuration.

The compounds of the formula (1) can be prepared by reacting a compound of the formula (2):

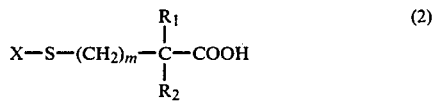

(2)

with compound (3):

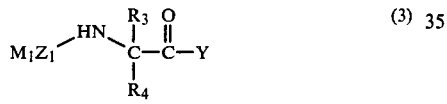

(3)

wherein the substituents are as defined hereinabove. The reaction can be carried out by converting compound (2) to the acid chloride by reaction with oxalyl chloride, and then adding compound (3). Alternatively, compounds (2) and (3) can be condensed directly, in the presence of a suitable coupling agent such as DCC (dicyclohexylcarbodiimide) or CDI (N,N'-carbonyldiimidazole) in a reaction familiar to those of ordinary skill in the peptide synthesis art. Condensation is preferred where X is hydrogen. For other X substituents, proceeding via a coupling agent is preferred where the reaction can proceed with a yield higher than that provided by the corresponding acid chloride route. The thermal

group can, if desired, be converted to hydrogen by hydrolysis with a mild acid. The above reactions proceed in a straightforward manner in a suitable solvent at temperatures ranging from 0° C. to 150° C.

The reaction products are sometimes obtained as a mixture of diastereoisomers which can be separated by standard methods of fractional crystallization or chromatography.

The compounds of this invention form salts, which are also within the scope of the invention, with various inorganic and organic acids and with alkali metals and alkaline earth metals such as potassium and calcium. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin-to-angiotensin I-to-angiotensin II sequence inhibit angiotensin I converting enzyme and therefore are useful in reducing or relieving hypertension. Furthermore, the compounds within the scope of the present invention which possess diuretic activity promote relief from hypertension by promoting diuresis, and consequently have utility in treating congestive heart failure. Compounds within the scope of the present invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs fo oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE I

To a mixture containing 100.0 gm (0.751 mol) of aminoacetaldehyde diethyl acetal and 101.7 gm (1.01 mol) of triethylamine in 250 ml of tetrahydrofuran at 0° C. and under an atmosphere of nitrogen was added dropwise over a 25 minute period 137.4 gm (0.823 mol) of ethyl bromoacetate. The ice bath was removed and the reaction mixture stirred at room temperature. After 19 hours the mixture was filtered and concentrated in vacuo. The residue was taken up in ether and washed twice with water and once with brine. It was dried over magnesium sulfate, filtered, and concentrated in vacuo. The residue was chromatographed via HPLC [Water's 500, 50% ether in hexanes, k'=2.0] to give 56.0 gm (34%) of compound (I-A), ethyl N-(2,2-diethoxyethyl)-glycinate, as an oil.

A mixture of 55.8 gm (0.254 mol) of ethyl N-(2,2-diethoxyethyl)glycinate, 50.7 gm (0.177 mol) of 1-amino-3-chloro-4,6-benzenedisulfonamide, and 250 ml of 7.2N aqueous hydrochloric acid in 400 ml of ethanol was refluxed for 3 hours. The mixture was cooled to 0° C. and the precipitate collected and washed twice with hot ethyl acetate, three times with hot ethanol, and three times with ether. The product was dried under vacuum to afford 30.0 gm (38%) of compound (I-B), 6-chloro-3,4-dihydro-3-[N-(ethoxycarbonylmethyl)aminomethyl]-7-sulfamoyl-2H-1,2,4-benzothiadiazine-1,1-dioxide hydrochloride as a white solid: mp 209°–211° C. (dec).

To a mixture containing 12.31 gm (75.9 mmol) of 3-acetylthio-2-methylpropionic acid in 10 ml of methylene chloride at room temperature and under an atmosphere of nitrogen was added dropwise over 35 minutes a solution of 12.25 gm (75.5 mmol) of N,N'-carbonyldiimidazole in 100 ml of methylene chloride. After 30 minutes a solution containing 16.96 gm (37.7 mmol) of 6-chloro-3,4-dihydro-3-[N-(ethylcarbonylmethyl)aminomethyl]-7-sulfamoyl-2H-1,2,4-benzothiadiazine-1,1-dioxide hydrochloride and 10.5 ml (75.3 mmol) of triethylamine in 10 ml of methylene chloride was added dropwise over a 20 minute period to the reaction mixture. After stirring at room temperature for 21 hours the mixture was acidified by the addition of 30 ml of 9N ethanolic hydrogen chloride. The mixture was concentrated in vacuo and the residue washed twice with ether. It was filtered through 175 gm of silica gel [23×4.3 cm, acetone] to yield 6.7 gm (37%) of the crude product which could be chromatographed via HPLC [Water's 500, 5% ethanol in methylene chloride, k'=4.0] to yield compound (I-C), 6-chloro-3,4-dihydro-3-[N-(ethoxycarbonylmethyl)-N-(3-acetylthio-2-methylpropanoyl)aminomethyl]-7-sulfamoyl-2H-1,2,4-benzothiadiazine-1,1-dioxide as a white solid: mp 127°–130° C.

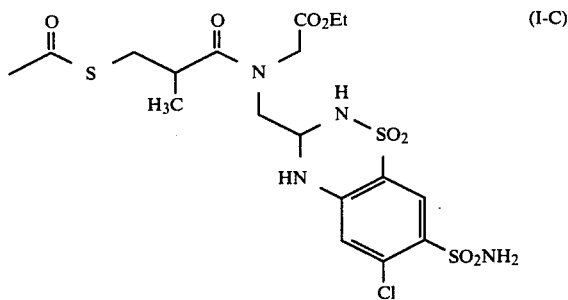

EXAMPLES II–VIII

The following compounds are made by analogous procedures familiar to those of ordinary skill in this art:

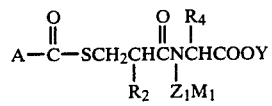

| COMPOUND | A | Y | R$_2$ | R$_4$ | Z$_1$ | M$_1$ |
|---|---|---|---|---|---|---|
| II | CH$_3$ | H | CH$_3$ | H | —CH$_2$— | |
| III | CH$_3$ | H | CH$_3$ | H | —CH(CH$_3$)— | |
| IV | C$_6$H$_5$ | H | CH$_3$ | H | —(CH$_2$)$_3$— | |
| V | (CH$_3$)$_3$CCH$_2$ | H | —(CH$_2$)$_4$NH$_2$ | H | —CH$_2$— | 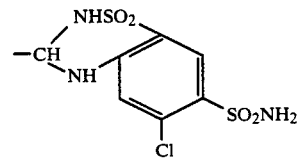 |

-continued $$A-\overset{O}{\underset{}{C}}-SCH_2\underset{R_2}{\overset{}{C}H}\overset{O}{\underset{}{C}}\underset{Z_1M_1}{\overset{R_4}{N}CHCOOY}$$

| COMPOUND | A | Y | $R_2$ | $R_4$ | $Z_1$ | $M_1$ |
|---|---|---|---|---|---|---|
| VI | $C_6H_5$ | H | $CH_3$ | H | $-(CH_2)_2-$ | 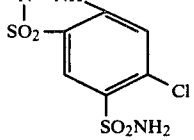 |
| VII | $CH_3$ | H | $CH_3$ | H | $-(CH_2)_2-$ | 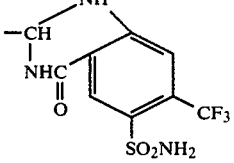 |
| VIII | $CH_3$ | H | $CH_3$ | H | $-(CH_2)_2-$ | 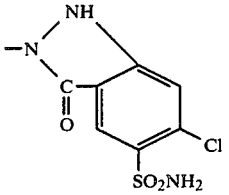 |

These compounds are:

II. 6-Chloro-3,4-dihydro-3-[N-(carboxymethyl)-N-(3-acetylthio-2-methylpropanoyl)-aminomethyl]-7-sulfamoyl-2H-1,2,4-benzothiadiazine-1,1-dioxide.

III. 6-Chloro-3,4-dihydro-3-[N-(carboxymethyl)-N-(3-acetylthio-2-methylpropanoyl)-1-aminoethyl]-7-sulfamoyl-2H-1,2,4-benzothiadiazine-1,1-dioxide.

IV. 6-Chloro-3,4-dihydro-3-[N-(carboxymethyl)-N-(3-benzoylthio-2-methylpropanoyl)-3-aminopropyl]-7-sulfamoyl-2H-1,2,4-benzothiadiazine-1,1-dioxide.

V. 6-Chloro-3,4-dihydro-3-[N-(carboxymethyl)-N-(2-(3,3,3-trimethylpropanoylthiomethyl-6-aminohexanoyl)aminomethyl]-7-sulfamoyl-2H-1,2,4-benzothiadiazine-1,1-dioxide.

VI. 2,3-Dihydro-2-[N-(carboxymethyl)-N-(3-benzoylthio-2-methylpropanoyl)-2-aminoethyl]-6-sulfamoyl-5-chloro-1,2,3-benzothiadiazole-1,1-dioxide.

VII. 7-Trifluoromethyl-1,2-dihydro-2-[N-(carboxymethyl)-N-(3-acetylthio-2-methylpropanoyl)-2-aminoethyl]-6-sulfamoyl-3H,4H-quinazoline-4-one.

VIII. 1,2-Dihydro-2-[N-(carboxymethyl)-N-(3-acetylthio-2-methylpropanoyl)-2-aminoethyl]-5-sulfamoyl-6-chloro-3H-indazole-3-one.

What is claimed is:

1. A compound of the formula

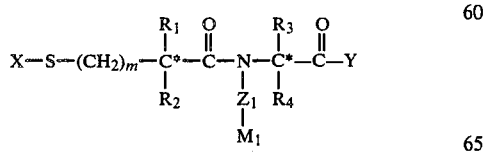

or a pharmaceutically acceptable salt thereof, wherein X is hydrogen or $$A-\overset{O}{\underset{}{C}}-$$

wherein A is $C_{1-7}$ alkyl, phenyl, or phenyl substituted with up to 3 substituents selected from the group consisting of halo, $C_{1-7}$ alkyl, $-CF_3$, $-OH$, $-COOH$, $-NH_2$, $-SO_2NH_2$;

m is 0 to 3 inclusive;

Y is $-OR$ or $-N(R)R$;

$R_1$, $R_2$, $R_3$ and $R_4$ are independently R or amino-$C_{1-7}$ alkyl;

$Z_1$, reading toward the $M_1$ substituent, is selected from the group consisting of $-(CH_2)_n-$, $-N(R)CH_2(CH_2)_n-$, $-N(R)CH_2(CH_2)_nNH-$, $-(CH_2)_nSO_2-$, $-(CH_2)_nN(R)SO_2-$, $-(CH_2)_n-N(R)-$, $-(CH_2)_nN(R)C(O)-$, $-(CH_2)_n-C(O)N(R)-$, or $-(CH_2)_nC(O)-$, in which n is 0 to 6 inclusive, and one of the $(CH_2)$ groups can be mono- or disubstituted with methyl or ethyl;

$M_1$ is benzothiadiazole having two or three substitutents selected from the group consisting of halogen, alkyl, aminoalkyl, aralkyl, cycloalkyl, alkylamino, acylamino, acylaminoalkyl, acylaminoalkylamino, trifluoromethyl, nitro, cyano, $-OR$, $-SR$, $-C(O)OR$, $-S(O)R$, $-SO_2R$, $-C(O)N(R)R$, $-N(R)R$, or $-SO_2N(R)R$;

wherein in each occurrence R is independently hydrogen, alkyl, cycloalkyl, aryl, aralkyl, heteroalkyl, heteroaralkyl, or heteroaryl;

wherein the alkyl groups and moieties have 1 to 7 carbon atoms, and the cycloalkyl, heteroalkyl, aryl and heteroaryl groups and moieties are selected from the group consisting of cyclopropyl, cyclobutyl, cyclopentyl, cyclohexyl, cycloheptyl, adamantyl, norbornyl, phenyl, tolyl, benzyl, phenethyl, indoyl, indolinyl, hydroxybenzyl, indanyl, naphthyl, tetrahydronaphthyl, decanhydronaphthyl, pyridyl, quinolyl, isoquinolyl, guanidino, pyrrolidyl, pyrrolyl, morpholinyl, furyl, furfuryl, tetrahydrofurfuryl, benzimidazolyl, thienyl, imidazolyl, and tetrahydroisoquinolyl.

2. Compounds and salts according to claim 1 wherein Y is hydroxy, lower alkoxy, —$NH_2$ or benzyloxy.

3. Compounds and salts according to claim 1 wherein $R_1$, $R_2$, $R_3$ and $R_4$ are independently hydrogen, lower alkyl, or amino-lower akyl.

4. Compounds and salts according to claim 2 wherein at least two of $R_1$, $R_2$, $R_3$ and $R_4$ are hydrogen.

5. Compounds and salts according to claim 1 wherein $Z_1$ is —$(CH_2)_n$— wherein n is 0 to 6.

6. Compounds and salts according to claim 1 wherein
m is 1 to 3;
Y is hydroxy, alkoxy having up to 4 carbon atoms, or benzyloxy;
$R_1$ and $R_3$ are hydrogen;
$R_2$ and $R_4$ are independently hydrogen or alkyl having up to 4 carbon atoms which is optionally substituted with amino; and
$Z_1$ is —$(CH_2)_n$— wherein n is 0 to 6.

7. The compound according to claim 6 which is 2,3-dihydro-2-[N-(Carboxymethyl)-N-(3-benzoylthio-2-methylpropanoyl)-2-aminoethyl]-6-sulfamoyl-5-chloro-1,2,3-benzothiadiazole-1,1-dioxide, and its pharmaceutically acceptable salts.

8. A compound or salt according to claim 1 having one or more asymmetric centers each of which is in the (S) configuration.

9. A compound or salt according to claim 6 having one or more asymmetric centers each of which is in the (S) configuration.

10. A pharmaceutical preparation comprising a compound or salt according to claim 1, in an amount effective to alleviate hypertension in a subject suffering therefrom, in association with a pharmaceutically acceptable carrier.

11. A method of treating hypertension comprising administering to a subject suffering therefrom a compound or salt according to claim 1 in an amount effective to alleviate said hypertension.

* * * * *